United States Patent [19]

Williamson et al.

[11] 4,434,672

[45] Mar. 6, 1984

[54] SAMPLING DEVICE

[76] Inventors: Vivien R. Williamson, 3 Colchester Rd., White Colne, Essex; Peter C. Deeks, 24 Nunns Meadow, Gosfield, Essex, both of England

[21] Appl. No.: 319,276

[22] Filed: Nov. 9, 1981

[30] Foreign Application Priority Data

Nov. 14, 1980 [GB] United Kingdom ............... 8036703

[51] Int. Cl.³ .......................................... G01N 35/08
[52] U.S. Cl. ............................. 73/864.22; 73/864.23; 422/64; 422/100
[58] Field of Search .......... 73/864.21, 864.22, 864.23, 73/864.24, 864.25, 864.01; 422/63, 64, 100; 436/49, 180; 141/115, 91

[56] References Cited

U.S. PATENT DOCUMENTS

| 3,134,263 | 5/1964 | de Jong | 73/864.25 |
| 3,635,094 | 1/1972 | Oberli | 73/864.24 |
| 3,719,086 | 3/1973 | Bannister et al. | 73/864.22 |
| 3,949,615 | 4/1976 | Stein et al. | 73/864.22 |
| 4,294,127 | 10/1981 | Tomoff | 73/864.25 |

Primary Examiner—Gerald Goldberg
Assistant Examiner—John E. Chapman, Jr.
Attorney, Agent, or Firm—W. S. Zebrowski

[57] ABSTRACT

A sampling device for automatic analysis apparatus in which a probe is movable along a single circular arc between a sample take-up position and a wash and/or standard solution take-up position. A wash/standard solution is delivered to the probe tip at the latter position via a vertically arranged tube. A pump is provided to pump solution up through the top of the tube and the tip of the probe contacts the surface of the meniscus formed for aspiration of a portion of the solution.

12 Claims, 4 Drawing Figures

SAMPLING DEVICE

FIELD OF THE INVENTION

Sampling devices for automatic analysis apparatus are used to withdraw aliquots of a sample, for example, blood, for transmission to the analysis apparatus for detection of, for example, elements such as potassium and sodium or dissolved gases.

BACKGROUND OF THE INVENTION

Most sampling devices which are designed to withdraw sample aliquots from successive sample specimens suffer from problems associated with the contamination of one sample specimen by material from a previous specimen.

This contamination arises as a result of sample material being deposited into a specimen by the sampling device itself, and of material remaining in the internal passageways of the sampling and analysis systems. To minimize this sample to sample contamination or "carryover" a number of sampling mechanisms have in the past been developed which provide for sampling of a wash solution between successive samples.

Furthermore, most analysis apparatus are essentially comparators and require the introduction of liquid calibration standards to ensure accuracy and to check their performance.

It is desirable that these standard solutions are introduced through the same path as any subsequent sample to be measured so that any pecularities of the system are common to both standard and samples. The method of measurement will then remove any such pecularities by relating the sample measurement to the standards measurement.

Previous sampling systems have used devices employing rotating or sliding valves at the input to the analysis apparatus to interchange the transmission of standard solutions and samples, or a probe arrangement that moves in two planes alternating between a receptacle containing the standard solution and/or a receptacle containing wash solution and the sample receptacle.

Valves and comparable mechanical devices are complicated, require precise machining and need a great deal of power to operate them. In addition, with the use of moving parts, failure of the seals is frequent, resulting in contamination of the standard with samples and vice versa. Furthermore, in the rotating valve system, the sample, wash and standard solutions do not follow the same path into the analysis apparatus.

Known probe arrangements have a relatively complicated mechanism to drive the probe between the sample and the wash solution receptacles and to move the probe into and out of these receptacles. In addition, contamination between the standard solution and the samples can occur since the probe is required to dip into a bulk of liquid. Thus, transference and hence contamination takes place between receptacles via the outside of the probe.

It is an object of the present invention to provide a sampling device which has a probe movable by means of a simple mechanism between a sample take-up position and a wash/standard solution supply.

It is a further object to provide a device having means to supply a flowing wash solution and/or a standard solution to the tip of a probe for up-take thereby.

BRIEF SUMMARY OF THE INVENTION

According to the present invention there is provided a sampling device comprising a source of suction, a probe having a passage connected to the suction source whereby a liquid sample can be aspirated into said passage by suction from said source, said probe being movable so that its tip can be located at a first position in which said passage can receive said sample and a second position, and means for delivering a wash/standard solution to said probe while it is in said second position, said means comprising a vertically arranged tube; solution supply means connected with the lower end of said tube for supplying solution to the top of the tube, and solution drain means arranged beneath the top of the tube for collection and removal of excess solution overflowing the top of the tube.

The probe is preferably mounted so that its tip describes a circular arc in a substantially vertical or, alternatively a horizontal plane, in moving between the sample take-up and wash/standard solution take-up positions.

According to a further aspect of the invention there is also provided a method of supplying a liquid for take-up by a probe for calibration and/or washing purposes comprising the steps of supplying liquid to a vertically arranged tube at a rate sufficient to maintain a meniscus at the top of said tube, draining away liquid overflowing the top of the tube and contacting the tip of said probe with the surface of the meniscus to take-up a portion of said liquid.

In a preferred embodiment of the invention, a single liquid is supplied to the probe in a continuous or intermittent stream to perform the function of both a wash solution and a standard solution.

Thus, an advantage of the embodiment of the sampling device of the present invention in which the probe moves in a single plane and requires no valve system for its operation over those already known, is that the mechanism of the device can be simple. Also the power required to operate the device may be kept extremely low and hence the device may be easily adapted to semi-automatic usage, or integrated into a completely automated system.

Furthermore, the embodiment of the liquid delivery means of the further aspect of the present invention eliminates the problem of contamination with sample liquid of the standard solution by the probe, since the outside of the probe tip is washed by the flowing standard solution.

Also, devices employing these liquid delivery means do not require very precise positioning of the probe with respect to the issuing liquid and hence do not have to be manufactured within very tight tolerances allowing manufacturing costs to be kept reasonably low.

DESCRIPTION OF PREFERRED EMBODIMENTS

Figure 1:
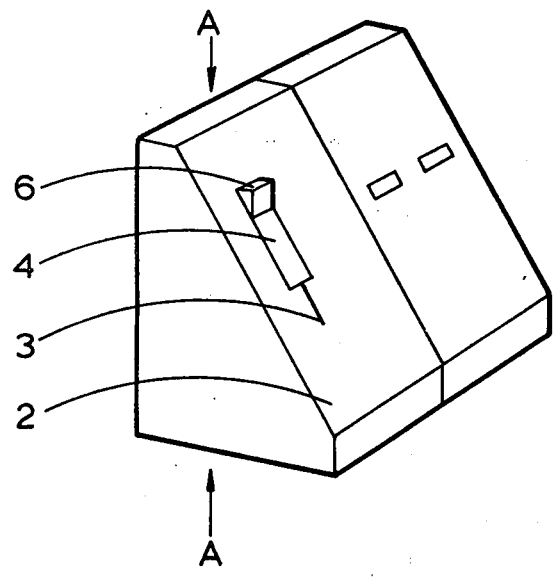
FIG. 1 shows a perspective view of an automatic analysis instrument incorporating an embodiment of a sampling device according to the present invention.
Figure 2:
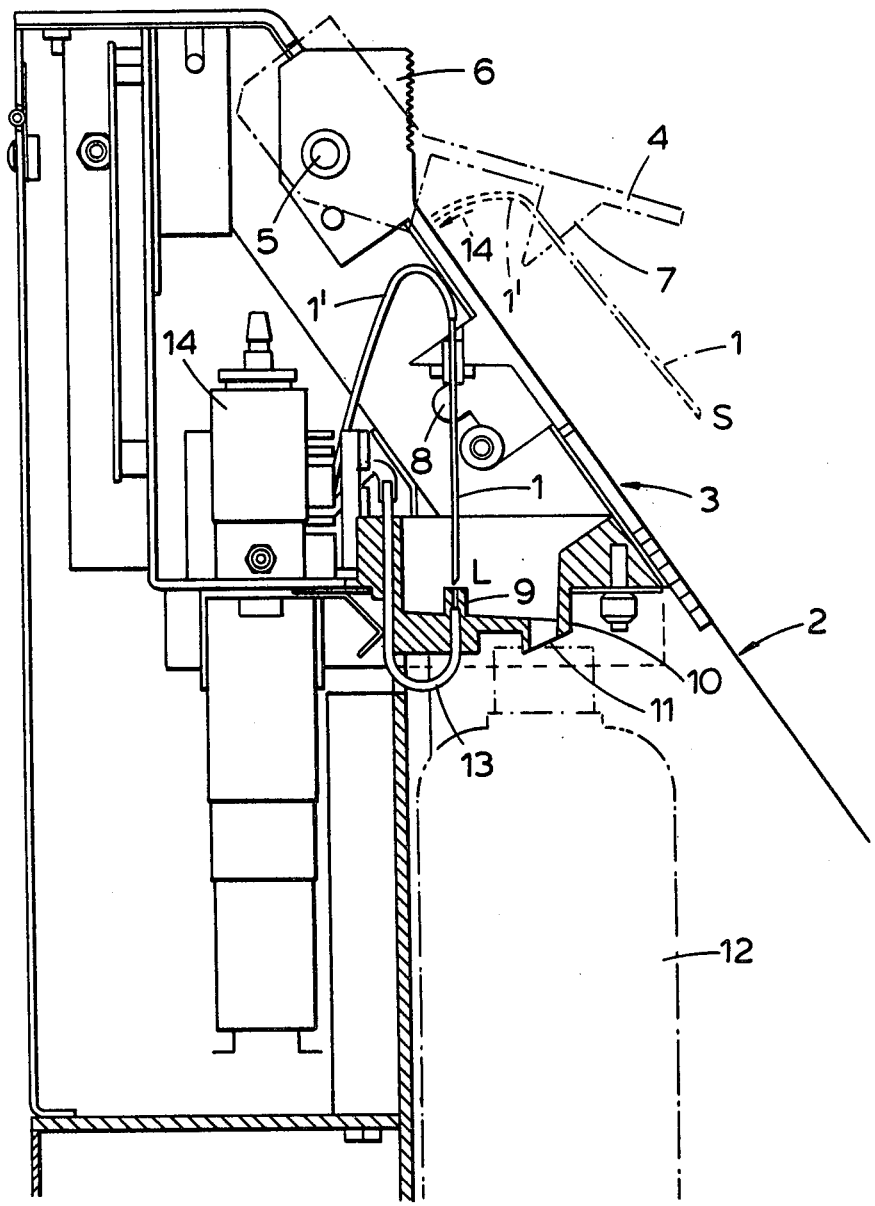
FIG. 2 shows a schematic section through the instruments shown in FIG. 1, along line A—A to show the embodiment according to the present invention.

In FIGS. 1 and 2, an analysis instrument is shown incorporating both a sample analysis apparatus and a sampling device according to an embodiment of the present invention. The sampling device comprises a sample probe 1. In FIG. 2, the probe 1 is illustrated by dashed and solid lines in its two extreme positions, a sample take-up position S and a wash/standard solution take-up position L respectively. The probe is movable between these two extreme positions either manually or by means of a motor, the probe tip describing a circular arc within a single vertical plane.

The device has a housing 2 whose wall is provided with a slot 3 through which the probe 1 can pass outside the housing to the sample take-up position S. An upper portion of this slot 3 is provided with a cover plate 4 which is mounted at the top of an axle 5, for pivotal movement between a fully open and a closed position. The probe 1 is rigidly mounted to a projection 7 on the reverse side of the cover plate 4. Thus rotation of the cover plate 4 about its axle 5 between its fully open and closed positions brings about the movement of the probe 1 from the sample take-up position S to the wash/standard take-up position L. A shaped member 6 is mounted co-axially with and rigidly to the cover plate 4 and extends through a hole in the housing wall to the outside. This member 6 serves as a push-button for manual rotation of the cover 4, to bring the probe 1 from the wash/standard to the sample take-up position, and also as a stop device which, by engaging the top and bottom walls of the housing, limits the rotation of the cover 4 between its two extreme positions. The probe may be taken from position S to position L by pressing the cover member to its closed position, where the probe abuts a pin member 8. Alternatively, a motor (not shown) coupled to the axle 5, may be operated to turn the axle 5 for positioning the probe 1.

The probe 1 is connected with a pump of the analysis apparatus by means of a flexible tube 1' for aspiration of sample or wash/standard solution by the probe into the analysis apparatus.

At position L the probe 1 is located directly above the top of a vertical tube 9 of a liquid supply device. The tube 9 is located in the base of a container 10 which has a drain hole 11 below which a waste bottle 12 is arranged. A pipe 13 enters the base of tube 9 through the base of the container 10. Liquid is supplied to the tube 9 via this pipe 13 from a supply bottle by means of a variable flow pump 14 so that a meniscus is formed at the top of the tube 9, and an overflow of liquid flows into the container 10 and is drained away. The bore of the drain hole 11 is greater than that of the tube 9 in order to prevent overflow of liquid from the container 10. A waste sample/solution pipe 15 also drains into the container 10 from the analysis apparatus.

Figure 3:
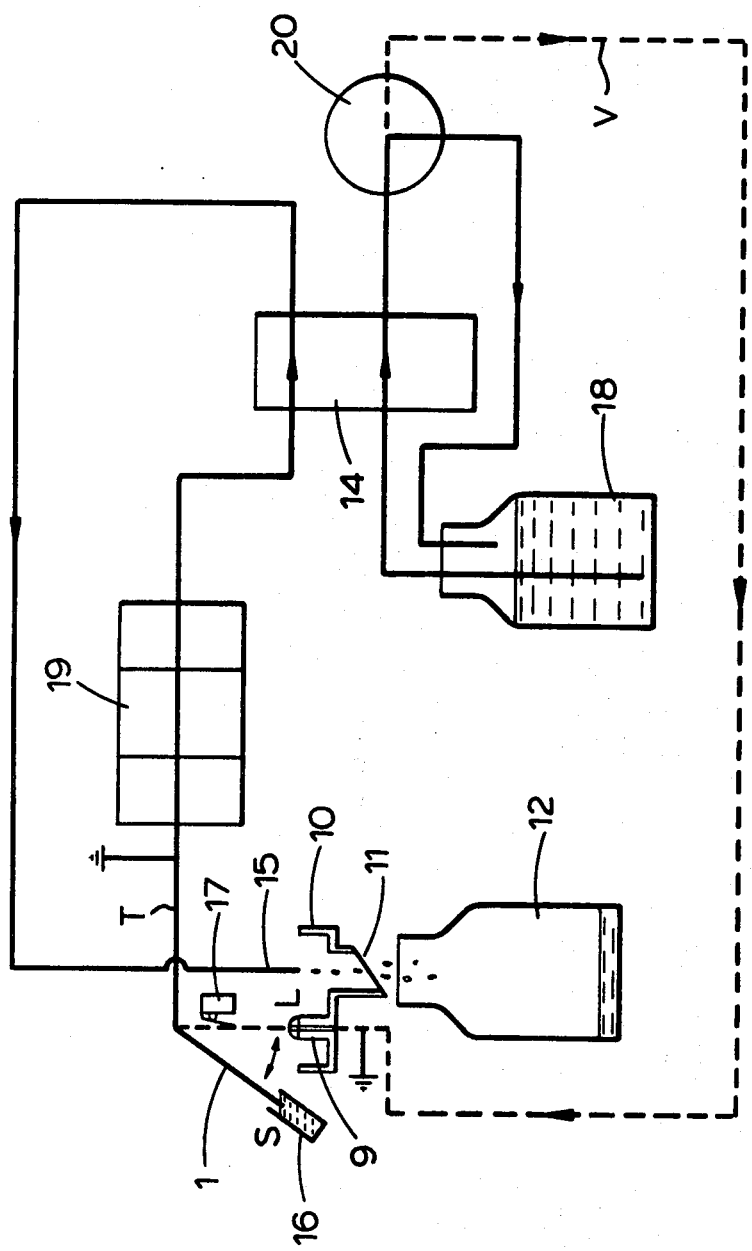
FIG. 3 shows a schematic diagram of an automatic analysis system incorporating an embodiment of the sampling device according to the present invention, and, FIG. 4 shows a further embodiment of a device of the present invention.

FIG. 3 illustrates schematically the system of an analysis instrument incorporating a sampling device according to the invention. The probe 1 is illustrated in the sample take-up position S. A sample specimen in a receptacle 16 is brought to the probe 1 and raised so that the tip of the probe dips into the sample liquid. A predetermined quantity of the sample is aspirated via the probe into path T of the analysis apparatus by means of the analysis apparatus pump 14 and is presented to ion sensitive electrodes 19 for analysis. These electrodes determine, for example, the sodium and potassium content of the sample against a reference value. The results obtained are then displayed digitally and/or presented in a print-out. After analysis, the sample is emptied from the analysis apparatus into the waste bottle 12 via the container 10.

When the probe 1 is in position L vertically above the tube 9, the probe 1 comes into contact with a switch 17 which causes the pumping of a standard solution from a standard/wash bottle 18 along dashed path V into the tube 9. The probe aspirates the solution into path T of the analysis instrument to wash this path, the waste solution draining into the waste bottle as before. The solution is supplied at a high rate in order to wash any sample liquid from the outside of the probe 1. A solenoid 20 may then be momentarily switched either manually or automatically into operation to return the pumped standard solution via a by-pass loop to the standard/wash bottle 18. As a result, the flow at the top of the tube 9 subsides and the probe 1 aspirates air into path T. This intermittent pumping of liquid segments with air samples therebetween provides an additional cleansing action to prevent contamination of the walls of the passages of the analysis apparatus by a sample.

After each or a predetermined number of sample and wash sequences the analysis instrument may be calibrated with the solenoid 20 switched so that the standard solution is again supplied to the top of the tube 9. However, in this case the rate of pumping is reduced so that the overflow rate from the tube is low thereby forming a meniscus. The probe 1 then aspirates a predetermined quantity of the standard solution which is carried along path T and is presented to the ion selective electrodes for calibration of the analysis apparatus, and thereafter drains into the waste bottle 12.

Other stations may be provided similar to the take-up position L, to enable introduction of, for example, other value standards into the analysis system. Thus, for example, the tube 9 supplying a single liquid for both wash and calibration purposes may be replaced by a plurality of such tubes supplying different liquids for washing and/or calibration between which the probe might be moved. Alternatively, these liquid sources may be moved in turn under the probe located at a single position.

The probe 1 shown in FIGS. 2 and 3 is mounted for movement in a circular arc in a vertical plane. However, as an alternative, the probe may be mounted on a horizontal slide device on which the probe may be moved back and forth between the sample and wash/standard take-up positions S and L.

Figure 4:
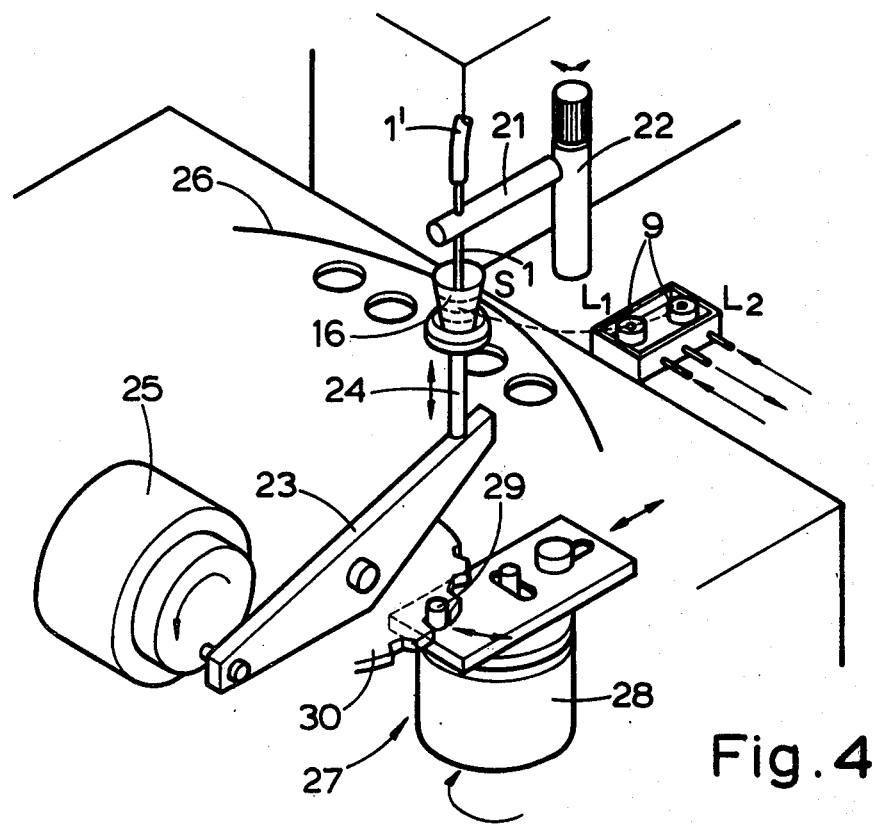

FIG. 4 shows a further embodiment of the sampling device according to the invention in which the tip of the probe 1 moves in a single horizontal plane between the sample take-up position S and two wash/standard take-up positions $L_1$, $L_2$. The probe is mounted on an arm 21 which extends horizontally from a vertical axle 22. Rotation of the axle 22 either manually or by means of a motor takes the probe 1 between these take-up positions.

As before with the probe 1, at the sample take-up position, the sample receptacle 16 is raised into position so that the probe tip dips into the sample specimen. In this embodiment of the sampling devices, there is shown a turntable 26 having holes near its circumference for receiving a sample receptacle 16. A pivotal rocker device 23 has a vertically projecting rod 24 at one end and is connected at the other, to a drum 25 at a distance from its rotational axis. Rotation of the drum 25 is translated into an up and down movement of the rod 24, which acts to raise and lower sample receptacles 16 to place their contents at the sample take-up position S.

This raising and lowering of the sample receptacle 16 is synchronised with rotation of the turntable 26 by a turntable drive 27 having a shaft 28. Rotation of the shaft 28 brings an eccentrically disposed projection 29 into engagement with a toothed wheel 30 for a portion of a revolution of the shaft, causing the wheel 30 and hence the turntable 26, to which it is connected, to rotate through an angle sufficient to bring a succeeding sample receptacle 16 into position below the sample take-up position S.

At the calibrate/wash station, the two wash/standard take-up positions are each supplied by a tube 9 located in a container 10 in a manner similar to that described above in connection wih FIGS. 1 to 3.

In this case a blank solution, eg water, is supplied to position $L_1$ and a standard solution to position $L_2$ and the probe moves between these two positions before proceeding to the sample take-up positions for sampling.

What is claimed is:

1. A sampling device comprising a source of suction, a probe having a passage connected to the suction source whereby a first solution comprising liquid sample can be aspirated into said passage by suction from said source, said probe being movable so that its tip can be located at a first position in which said passage can receive said sample and a second position, and means for delivering a second solution to said probe while it is in said second position, said means comprising a vertically arranged tube which is substantially coaxial with said probe when said probe is in said second position, the upper end of said tube being beneath but sufficiently close to the tip of said probe in said second position that the tip of said probe extends into a meniscus that forms at the top of said tube when said second solution overflows said tube, solution supply means connected with the lower end of said tube for supplying solution to the top of the tube, and solution drain means arranged beneath the top of the tube for collection and removal of excess solution overflowing the top of the tube.

2. A device as claimed in claim 1 wherein said second solution comprises a wash solution.

3. A device as claimed in claim 1 wherein said second solution comprises a standard solution.

4. A device as claimed in claim 1 wherein said solution supply means comprises a solution reservoir, a pump connected with said reservoir for pumping solution from the reservoir to the tube and switching means located downstream of the pump which operates to temporarily divert the pumped solution from the tube so as to interrupt delivery of the solution to said second position.

5. A device as claimed in claim 1, wherein the probe is mounted so that its tip moves only in a circular arc in a substantially vertical plane in moving between said first and second positions.

6. A device as claimed in claim 1, wherein said solution delivering means comprises a plurality of vertically arranged tubes and a plurality of solution supply means are connected with the lower ends of said tubes for supplying solution to the top of said tubes and the solution drain means is arranged beneath the top of the tubes for collection and removal of excess solution overflowing the top of the tubes, each of said tubes delivering solution to said probe while said probe is in an associated position.

7. A device as claimed in claim 1, wherein the probe is mounted so that its tip describes a circular arc in a substantially horizontal plane between said first and second positions.

8. A device as claimed in claim 1, further comprising means for transporting a sample receptacle containing a liquid sample to a position in which, while the probe tip in said first position, the said passage can receive said sample.

9. A device as claimed in claim 8, wherein the transport means comprise a turntable having a plurality of holes therein, each for receiving a sample receptacle first drive means for intermittently rotating said turntable, a member located beneath said turntable for engaging a sample receptacle to raise and lower that receptacle, and second drive means for said member which is synchronised with said first drive means.

10. A method of sampling a sample solution and supplying a liquid for take-up by a probe comprising the steps of aspirating said sample solution through said probe, supplying liquid to a vertically arranged tube at a rate sufficient to maintain a meniscus at the top of said tube, draining away liquid overflowing the top of the tube, contacting the surface of the meniscus with the tip of the said probe, and aspirating a portion of said liquid through said probe.

11. A method as claimed in claim 10 wherein the step of supplying a liquid to said tube is intermittent to provide additional cleansing action.

12. A method as claimed in claim 10 wherein the step of supplying a liquid to said tube is continuous.

* * * * *